United States Patent [19]

Samhaber et al.

[11] Patent Number: 4,695,551
[45] Date of Patent: Sep. 22, 1987

[54] SAMPLING APPARATUS FOR A BIOLOGICAL REACTOR

[75] Inventors: Wolfgang Samhaber; Werner Renn, both of Allschwil, Switzerland

[73] Assignee: Proton AG, Zug, Switzerland

[21] Appl. No.: 854,174

[22] Filed: Apr. 21, 1986

[30] Foreign Application Priority Data

May 4, 1985 [DE] Fed. Rep. of Germany ....... 3516080

[51] Int. Cl.[4] .............................................. C12M 1/26
[52] U.S. Cl. .................................... 435/292; 435/287; 435/291; 435/311; 73/863.23
[58] Field of Search ..................... 73/863.23; 210/359; 435/287, 291, 292, 293, 294, 299, 311

[56] References Cited

U.S. PATENT DOCUMENTS

| 3,830,106 | 8/1974 | Gardiner et al. | 73/863.23 |
| 3,841,488 | 10/1974 | Yessaian | 210/168 |
| 3,997,447 | 12/1976 | Breton et al. | 210/360 A |
| 4,315,990 | 2/1982 | Sheets | 435/291 |
| 4,404,284 | 9/1983 | Heider et al. | 435/291 |

FOREIGN PATENT DOCUMENTS

| 007133 | 1/1980 | European Pat. Off. | |
| 275426 | 7/1970 | U.S.S.R. | 73/863.23 |

OTHER PUBLICATIONS

"Continuous On Line Monitoring of Fermentation Processes", Dincer et al., from *Developments in Indust. Microbiol.* (1984).
"Measuring & Control of Fermentation Processes", Kempe et al., from *Process Biochemistry*, Dec. 1983.

*Primary Examiner*—Samuel Scott
*Assistant Examiner*—Allen J. Flanigan
*Attorney, Agent, or Firm*—Werner W. Kleeman

[57] ABSTRACT

The sampling apparatus for a biological reactor comprises a probe housing which is connectable to a connection port of a bioreactor. A probe located within the probe housing contains a head region having a semipermeable membrane which permits the passage or throughflow of culture filtrate, but does not allow the entrance of cells. In order to avoid clogging of the semipermeable membrane, this probe is connected with a vibrator which imparts or transmits to the semipermeable membrane a preferably continual vibrating motion which preferably acts in the axial direction of the probe.

13 Claims, 1 Drawing Figure

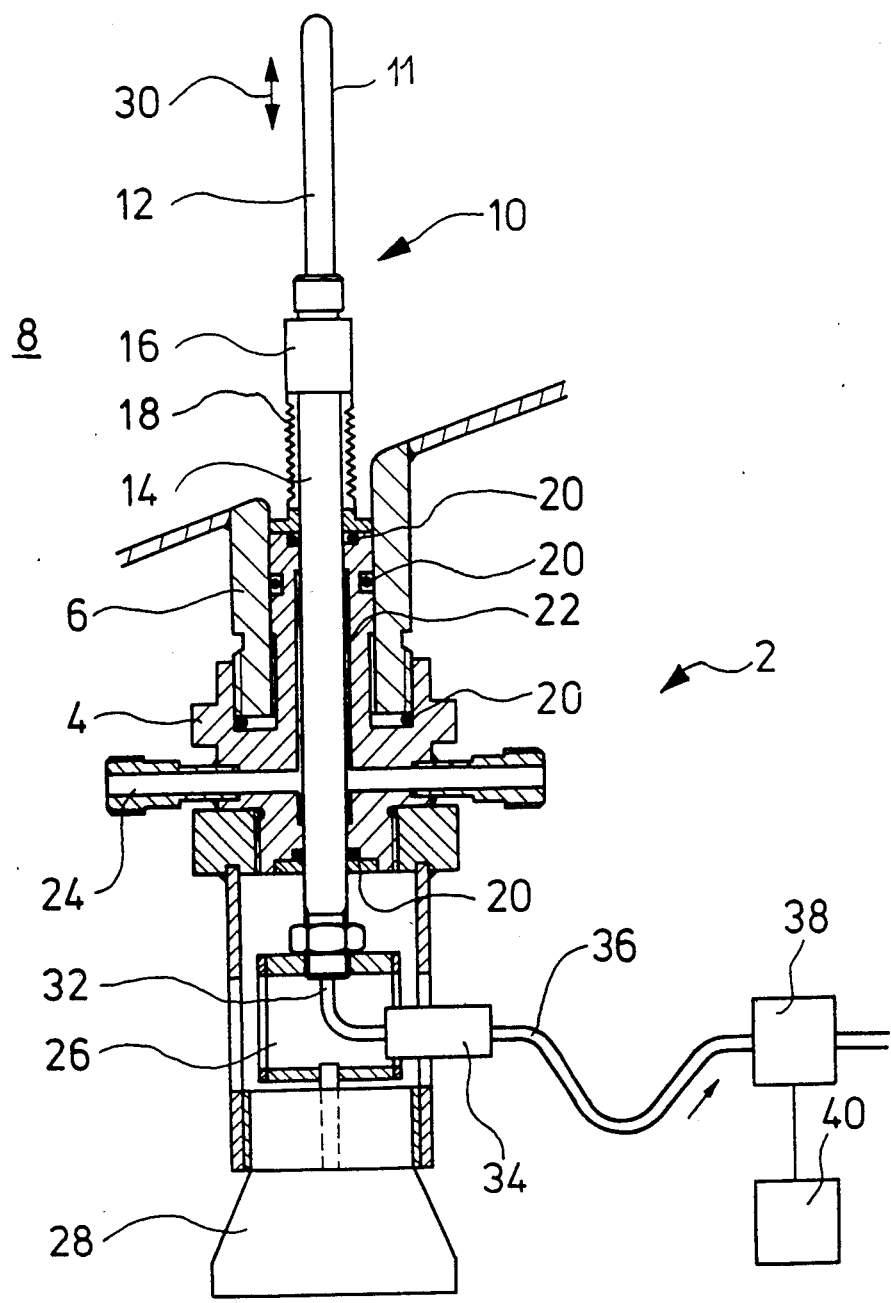
Figure

SAMPLING APPARATUS FOR A BIOLOGICAL REACTOR

BACKGROUND OF THE INVENTION

The present invention broadly relates to a sampling apparatus for biological reactors and which has a microfilter which is connectable with a bioreactor that is connected to a conduit or connection means for sampling.

Such sampling apparatus are especially provided for the determination of the presence of soluble substances such as nutrient media, metabolites and reaction products, and the concentrations thereof. The measurement of these parameters —aside from the already classical parameters such as temperature, pH-value, oxygen content, $CO_2$-content, and so forth - allows improved control of biological processes.

This trend is today further supported by the employment of microprocessors. This is, however, only possible if all measurements can be taken on-line in order to continuously and quickly be able to receive all measurement data which are necessary for process control. New means or devices have already been developed for specific parameters, such as, for example, enzyme electrodes or measurement probes with silicon membranes, which however, are very product-specific and are not directly usable in a bioreactor, partially for reasons of sterility.

In order to overcome this problem, a sampling apparatus of the previously mentioned type has recently been proposed in which continuous sampling is performed by means of a microfiltration system which is traversed by material in the reactor and which is connected to a measuring system.

A description of existing new systems can be found, for example, in:

A. Dincer et al (1984), Developments in Industrial Microbiology 25, page 603; and Kempe and Schallenberger (1983), Process Biochemistry, December, page 7.

A great disadvantage of the suggested sampling apparatus is that the sampling occurs or takes place in an external loop. This requires the construction of sampling systems with pumps, connection and return lines or conduits and separation devices which are especially developed for this purpose. In addition to this, the absolutely necessary sterilization of these external systems is problematic. Furthermore, the removed sample quantity is relatively large.

The employment of microfiltration membranes in situ in bioreactors has hitherto been described only for the continuous removal of the desired end products (cf. European Patent No. 7133-A).

SUMMARY OF THE INVENTION

Therefore, with the foregoing in mind, it is a primary object of the present invention to provide a new and improved construction of a sampling apparatus for a biological reactor which does not exhibit the aforesaid drawbacks and shortcomings of the prior art constructions.

Another and more specific object of the present invention aims at providing a new and improved construction of a sampling apparatus of the previously mentioned type which no longer has the problem of sterile in situ measurement of soluble substances in a bioreactor.

A further significant object of the present invention aims at providing a new and improved construction of a sampling apparatus of the character described which is relatively simple in construction and design, extremely economical to manufacture, highly reliable in operation, not readily subject to breakdown or malfunction and requires a minimum of maintenance and servicing.

Now in order to implement these and still further objects of the invention, which will become more readily apparent as the description proceeds, the sampling apparatus of the present invention is manifested by the features that it comprises a probe whose head region possesses a microfilter formed as a semipermeable membrane and the membrane is connected with a device or means for moving or vibrating the surface of the membrane.

These sampling apparatuses are preferably equipped or provided with connections made according to existing connection standards for bioreactors, such as, are for example, valid for probes for measuring pH-values, $pO_2$-values, $pCO_2$-values, and so forth. The available cross-sectional area of the sampling apparatus is relatively small due to this manner of construction. Consequently, the danger that substances settle or deposit on the membrane is greater according to the nature or character of the material in the bioreactor, thereby reducing the functional capability of the membrane. This problem is avoided by moving or vibrating the membrane, wherein the motion or vibration can take place intermittently or preferably continuously. Furthermore, this motion of the membrane can occur by means of rotation around its own axis or by means of a reciprocatory, i.e. oscillatory motion in a radial direction or in an axial direction. Axial motion is preferred since a suitable crossflow can be achieved through the membrane by reciprocatory motion with small amplitude at very high frequency with low expense. In this way the effect of the material in the reactor on the sampling process is kept small with optimal efficiency.

The advantages of the sampling apparatus are, for example:

(a) Application in standardized ports of existing bioreactors;

(b) High efficiency with insignificant influence of the material of the bioreactor;

(c) Continuous and very rapid determination of instantaneous substance values in the bioreactor;

(d) Sampling or removal of the actually required sample quantities which permit very exact measurements due to the minute dead volume of the probe; and (e) In situ sterilization.

Materials can be selected for the membrane which are permeable only to the desired substrate to be measured. Conventional membranes can be utilized such as, for example, symmetrical or asymmetrical membranes, polar or non-polar membranes, or hydrophilic or hydrophobic membranes which can be selected according to the character or nature of the soluble substances to be measured, and such membranes must be impermeable especially for the cultivated microorganisms, cells, et cetera. A membrane pore size of approximately 0.01 to 0.1 $\mu$m, for example, would be advantageous for proteins.

The sampling apparatus can not only serve for the extraction or sampling of individual samples but also for continuous sampling. Especially in the latter case, the withdrawn or extracted samples are preferably fed to a suitable on-line measurement system which is selected according to known principles. Individual components are, for example, those such as described in the aforesaid literature reference of A. Dincer et al and can, for example, be connected to a microprocessor control device.

The motion or vibration of the membrane can be achieved by means of a suitable apparatus for rotational or reciprocatory motion. A crossflow through the membrane of approximately 4 m/s can be achieved, for example, in the latter case with a motion or vibration of, for example, only 0.1 mm amplitude by utilizing an ultrasonic vibrator with a frequency of approximately 20 kHz.

BRIEF DESCRIPTION OF THE DRAWING

The invention will be better understood and objects other than those set forth above will become apparent when consideration is given to the following detailed description thereof. Such description makes reference to the single FIGURE of the drawing of a typical preferred embodiment of the invention wherein there is shown a section of a sampling apparatus mounted on a bioreactor.

DETAILED DESCRIPTION OF THE PREFERRED EMBODIMENT

Describing now the drawings, it is to be understood that to simplify the showing thereof only enough of the structure of the sampling apparatus for a biological reactor has been illustrated therein as is needed to enable one skilled in the art to readily understand the underlying principles and concepts of this invention. Turning now specifically to FIG. 1 of the drawings, the sampling apparatus 2 illustrated therein by way of example and not limitation will be seen to comprise a probe housing 4 which is detachably connected, for example is screwed on, to a connecting port 6 of a bioreactor 8. The sampling apparatus 2 contains a probe 10 which is displaceable in an axial direction in the probe housing 4. The probe 10 comprises a head region 11 having a semipermeable membrane 12 which is fastened to a section of pipe or tubing 14 that is movably arranged in the probe housing 4. The membrane 12 is connected to a clamp or fastener 16 of the section of pipe 14 and the clamp or fastener 16 is connected by means of a bellows 18 for sealing with the probe housing 4. The section of pipe 14 situated in the probe housing 4 is further sealed by means of sealing rings 20, such as O-rings. An annular chamber 22 enclosing the section of pipe 14 is provided in the probe housing 4 which is in contact with conduit connections 24 in order to form a sterilization barrier, for example by means of the passage of steam.

The end of the section of pipe 14 of the probe 10 opposite to the membrane 12 supports a further housing 26 by means of which the section of pipe 14 is connected with a vibrator 28 which imparts or transmits an axial vibrating motion 30 to the probe 10.

A conduit or connection means 32 is connected within the housing 26 to the section of pipe 14 which is connected by means of a coupling piece or member 34 with a flexible conduit 36 which leads to a measurement system 38. A microprocessor 40 is connected to the measurement system 38 and which processes the measured data of the measurement system 38 and thereby controls the process of the bioreactor 8 in a manner which is known per se and therefore need not be here further described. In lieu of the conduit 36 a not particularly shown stopcock or cutoff valve can be attached to the coupling piece 34 for the extraction of individual samples.

The components of the sampling apparatus 2 which are exposed to the inside of the bioreactor 8 are composed of materials which can withstand the conventional sterilization measures in a bioreactor.

The housing 26 is vibrated by means of the vibrator 28 during operation and these vibrations continue over the section of pipe 14 into the membrane 12 of the probe 10. A possible deposit, for example of cells, on the membrane 12 is thereby substantially prevented. The culture filtrate permeates through the membrane 12 and is led by means of the section of pipe 14, the conduit 32 and the conduit 36 to the measurement system 38 and there analyzed. The sealing rings 20 prevent the entrance of material from the bioreactor 8 into the sampling apparatus 2 or, conversely, maintain the inner sterility of the bioreactor 8.

While there are shown and described present preferred embodiments of the invention, it is to be distinctly understood that the invention is not limited thereto, but may be otherwise variously embodied and practiced within the scope of the following claims. ACCORDINGLY,

What we claim is:

1. A sampling apparatus for a bioreactor having a connection port, comprising:
   a probe having a head region operatively coacting with said bioreactor;
   said head region comprising a semipermeable membrane defining a microfilter;
   a conduit operatively coupled with said microfilter for sampling contents of the bioreactor;
   said semipermeable membrane having an outer surface;
   means operatively connected with said semipermeable membrane for moving said outer surface of said semipermeable membrane;
   a probe housing;
   said semipermeable membrane together with said probe being displaceably mounted in said probe housing;
   sealing means;
   said probe including a section of pipe having a first end and a second end;
   said sealing means sealingly interconnecting said section of pipe and at least part of said probe housing and sealing said probe housing from the contents of said bioreactor;
   a coupling housing;
   said section of pipe possessing on said first end said semipermeable membrane and on said second end said coupling housing;
   said coupling housing being connected with said means for moving said outer surface of said semipermeable membrane; and
   said conduit being connected to said section of pipe.

2. The sampling apparatus as defined in claim 1, wherein:
   said sealing means constitute bellows means.

3. The apparatus as defined in claim 2, further including:
   fastening means fastening said semipermeable membrane at said first end of said section of pipe; and said bellows means sealingly interconnecting said fastening means and said probe housing.

4. The sampling apparatus as defined in claim 1, wherein:

said means for moving said outer surface of said semipermeable membrane comprises a continuously active vibrator.

5. The sampling apparatus as defined in claim 1, wherein:

said probe has a longitudinal direction; and said moving means oscillating said semipermeable membrane in said longitudinal direction of said probe.

6. A sampling apparatus for a bioreactor having a connection port, comprising:

a probe having a head region operatively coacting with said bioreactor;

said head region comprising a semipermeable membrane defining a microfilter;

a conduit operatively coupled with said microfilter for sampling contents of the bioreactor;

said semipermeable membrane having an outer surface;

means operatively connected with said semipermeable membrane for moving said outer surface of said semipermeable membrane;

a probe housing;

said semipermeable membrane together with said probe being displaceably mounted in said probe housing;

sealing means;

said probe including a section of pipe having a first end and a second end;

said section of pipe being sealed by said sealing means and displaceably mounted in said probe housing;

a coupling housing;

said section of pipe possessing on said first end said semipermeable membrane and on said second end said coupling housing;

said coupling housing being connected with said means for moving said outer surface of said semipermeable membrane; and said conduit being connected to said second end of said section of pipe.

7. The sampling apparatus as defined in claim 1, wherein:

said semipermeable membrane is substantially permeable to soluble substances and substantially impermeable to cells.

8. The sampling apparatus as defined in claim 1, wherein:

said probe having a portion exposed to the interior of said bioreactor; and said exposed portion of said probe comprising a material which can withstand sterilization processes applied to said bioreactor.

9. The sampling apparatus as defined in claim 1, wherein:

a probe housing is detachably connectable to said connecting port of said bioreactor.

10. The sampling apparatus as defined in claim 9, wherein:

said probe housing has a connecting port; and said connecting port of said probe housing being standardized for measurement probes.

11. The sampling apparatus as defined in claim 1, wherein:

said probe is connectable to a measurement device.

12. The sampling apparatus as defined in claim 1, wherein:

said probe is connectable to a control device.

13. The sampling apparatus as defined in claim 1, wherein:

said probe is connectable to a measurement device and a control device.

* * * * *